United States Patent [19]

Falk et al.

[11] Patent Number: 4,881,824

[45] Date of Patent: Nov. 21, 1989

[54] IMMERSIBLE PROBE

[75] Inventors: Richard A. Falk, Ft. Lauderdale, Fla.; James Colzani, Menomonee Falls, Wis.

[73] Assignee: Midwest Instrument Co., Inc., Hartland, Wis.

[21] Appl. No.: 289,040

[22] Filed: Dec. 23, 1988

[51] Int. Cl.$^4$ .......................... G01K 7/02; G01K 1/08
[52] U.S. Cl. ...................................... 374/140; 266/88; 266/95; 136/234; 374/208; 374/139
[58] Field of Search .................. 374/139, 140, 208; 266/88, 95; 136/234

[56] References Cited

U.S. PATENT DOCUMENTS

| | | | |
|---|---|---|---|
| 2,785,216 | 3/1957 | Winner, Jr. | 374/208 |
| 3,201,277 | 8/1965 | Fish | 374/140 |
| 3,279,254 | 10/1966 | Zumbusch | 73/309 |
| 4,002,069 | 1/1977 | Takemura et al. | 374/140 |
| 4,401,389 | 8/1983 | Theuwis | 374/140 |
| 4,778,281 | 10/1988 | Falk | 374/140 |

FOREIGN PATENT DOCUMENTS

| | | | |
|---|---|---|---|
| 108431 | 4/1983 | European Pat. Off. | 374/139 |
| 61-213735 | 9/1986 | Japan | 374/139 |
| 1096499 | 12/1967 | United Kingdom | 374/139 |
| 1243028 | 8/1971 | United Kingdom | 374/140 |

Primary Examiner—William A. Cuchlinski, Jr.
Assistant Examiner—Diego F. F. Gutierrez
Attorney, Agent, or Firm—Fuller, Puerner & Hohenfeldt

[57] ABSTRACT

An immersion sampler probe for the analysis of a molten metal bath in a BOF vessel. The probe is weighted to penetrate the slag and position a temperature sensor or oxygen sensor at an appropriate depth. A counterweight with a float ensures proper immersion depth. The float keeps the lead wires from contacting the molten metal.

6 Claims, 1 Drawing Sheet

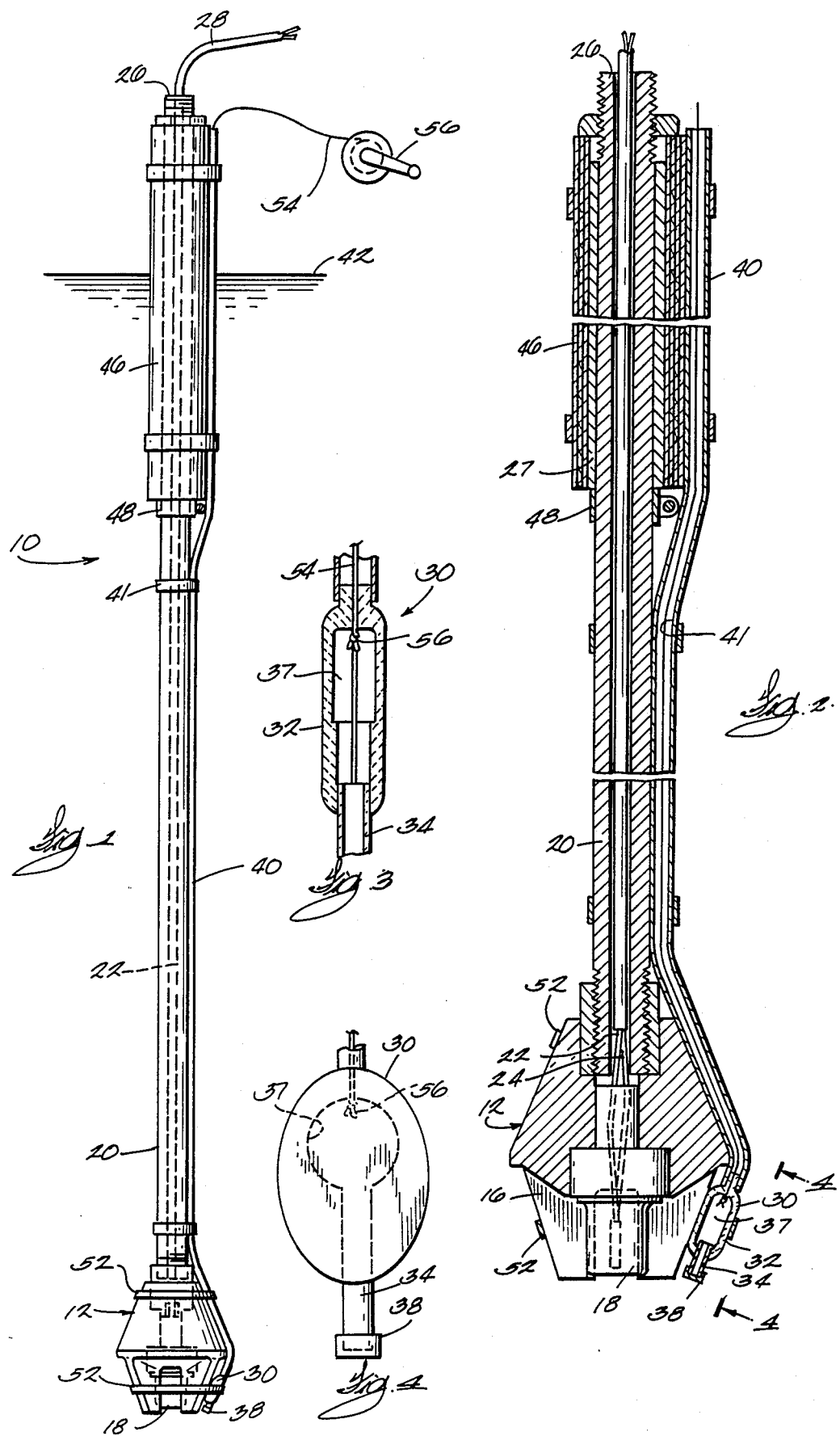

IMMERSIBLE PROBE

BACKGROUND OF THE INVENTION

In the manufacture of steel in basic oxygen type furnaces (BOF), measurements of bath temperature are desirably taken during the refining period so that adjustments can be made in the oxygen blowing time, rate and volume for the final bath chemistry, and temperature. During the oxygen blowing process the molten metal bath is very agitated by the blowing of oxygen beneath and onto the surface of the slag and metal. In order to obtain accurate and reliable temperature readings, temperature probes must be immersed well below the surface of the steel bath and steel/slag layer interface. A deep penetration into the steel bath prevents the temperature sensor from being blown around by the high volume high force oxygen discharge from the oxygen lance. Ideally, sensors should be immersed 6 inches or more into the bath below the interface.

Oxygen readings are desirable and possible after a controlled blow is finished or interrupted. Carbon content can be accurately calculated from metal bath oxygen content at levels below the 15% carbon range. Temperature is obtained by the thermocouple of the oxygen probe. The oxygen reading for free oxygen can be used for accurate and precise addition of deoxidation agents.

Using a reliable accurate in-blow temperature probe and oxygen temperature carbon and sample probe, through the BOF furnace aperture results in saving steel making time and furnace wear resulting in more production and better or equivalent quality at lower costs.

Because of the high density of the molten metal, it is difficult to push the probe beyond the slag layer and into the metal to sufficient depth because of the buoyancy afforded by the dense metal displaced by the probe. The most reliable method at the present involves the use of a very expensive sublance with motorized assembly to lower a pipe into the BOF vessel. Because of the expense of several million dollars assembling and installing this sublance equipment in a steel mill, it is not a desirable choice. It also is not a desirable choice because of new steel making procedures using ladle furnaces and ladle metallurgical stations. Accordingly, free falling bomb lances have been devised to weight a probe for immersion purposes. The Cole Patent 3,374,122 is an example of a weighted probe. The Ehrenberg Patent No. 3,497,398 is a further development of the bomb type probe. Patent No. 3,505,871 shows an additional type of immersion vehicle intended to be inserted in a BOF vessel.

These types of drop-in sensors, have not provided consistent and reliable results because of ineffective and inconsistent immersion depths below the slag layer especially while blowing oxygen. Typically there is not enough weight provided to overcome the buoyant force to obtain sufficient penetration for accurate and reliable "in blow" temperature readings and accurate "after blow" oxygen, carbon and temperature readings.

SUMMARY OF THE INVENTION

The invention provides an immersible drop-in sensor which is provided with a counterweight partially above the metal or slag to overcome the buoyancy of the submerged probe portions to achieve the proper penetration and depth beyond the slag and into the metal for reliable readings.

To accomplish this, the submersible weight or bomb weight has the fewest and the smallest possible cavities for the sensor and for the lead wires to minimize the volume of displaced molten metal which is caused by voids rather than high density metal. More specifically, the problem caused by the prior art drop-in probes is the failure to recognize that if the displaced volume of molten metal steel is significantly greater than the volume of the high density weight metal in the bomb, it will float rather than become immersed. This is because of the well known principle that the buoyant force on a body immersed in a fluid is equal to the weight of the fluid displaced by that object. If the buoyant force acting upward has a magnitude greater than the downward force exerted by gravity and ferrostatic pressure on the top of the submerged weight, it will float at the surface of the molten metal.

The invention attempts to overcome a large part of this buoyancy by reducing the size of cavities used for sensors and wires.

Because reducing the cavity size to minimize the volume of the displaced metal alone cannot overcome the buoyant upward force on the bomb, it is necessary to provide a counterweight above the surface of the molten metal and preferably the slag to accomplish and counter-balance the upward buoyant forces with a downward force. This counterweight can be in the form of a thick walled pipe. Throughout the construction of both the counterweight and the submersible weight, an effort is made to minimize the nonmetallic spaces or voids including the internal diameter of the counterweight pipe to maximize the weight-to-volume displacement ratio of the counter-weight. Accordingly, the smallest diameter thick-walled metal pipe is used. The length of the counter-weight pipe is selected to balance the weight of the displaced volume of metal due to the volume of the cavities in the submersed weight. The counterweight is kept above the slag where it is possible to minimize the weight of the displaced slag; approximately ¼ of the weight of molten steel. To ensure that the counterweight and probe are maintained in a vertical position, an adjustable float is provided adjacent the upper end of the elongated pipe which will provide a buoyant force on the upper end of the pipe to maintain the probe in the essentially vertical position in the vessel and also act as a floatation stop to limit vertical downward movement of the probe to a selected depth in the steel below the slag.

In addition, the invention can include a sample pod which is fastened to the submersible weight which contains a sample cavity and deoxidant for retrieving a sample of the bath. The sample pod can be in accordance with the "piggyback" samplers illustrated in U.S. Pat. No. 4,069,715, the entire disclosure of which is incorporated by reference. The sample pod can be constructed of a refractory fiber such as Babcock & Wilcox's "Kaowool" 2600 bulk fiber, which is 55% alumina and 44.9% silica. A fine braided wire made of stainless steel or the like, and protected by a paper tube or wrapping from the slag and steel is fastened to the vertical counterweight by paper tape and connected to the interior of the sample cartridge and formed into the steel sample. The paper tube provides venting for the sample receiving chamber. The wire enables retrieval of the sample when it is released in a few seconds of a fusible clamp and tape holding its refractory fiber protection pod and paper protection tube to the weight. Further objects, advantages, and features of the invention will become apparent from the drawings.

BRIEF DESCRIPTION OF THE DRAWINGS

FIG. 1 is a side elevational view and fragmentary section of a probe in accordance with the invention;

FIG. 2 is an enlarged view of the probe shown in FIG. 1 in fragmentary section;

FIG. 3 is an enlarged sectional view of the sampler shown in FIG. 2; and

FIG. 4 is an enlarged view of the sampler along line 4—4 of FIG. 2.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings (FIGS. 1-4), FIG. 1 shows a probe or lance 10 which includes at its lower end a weight 12 made of steel or iron and a cavity 14 between four spaced ribs 16 which are arranged at 90° with respect to each other. The ribs protect the measurement devices located in the cavity 14. The cavity 14 can be provided with a thermocouple assembly 18 or an oxygen sensor 18. The thermocouple assembly can be made in accordance with the disclosures in my U.S. Pat. Nos. 4,778,281 and 4,358,630. The oxygen sensor can be made in accordance with U.S. Pat. No. 3,723,279. The entire disclosures of said three patents are incorporated herein by reference. The first weight 12 is connected to a metal pipe 20 which desirably has a thick wall and a very small diameter for purposes hereinafter described. A second pipe 27 (FIG. 2) can be telescoped over the first pipe to add weight for purposes herein described. The electrical conductors or leads 22, 24 for the thermocouple extend through the pipe 20 and exit from the open end of the pipe at 26. The free ends of the leads 28 are suitably connected to appropriate instrumentation for either the thermocouple or oxygen sensor as is well known in the art.

The probe can be provided with an immersion sampler rod 30 (FIGS. 3 and 4) which contains an outer protective coating of refractory fiber material as described above or other material as described in my U.S. Pat. No. 4,659,679 and can be provided with two spaced clam shell mold halves 32 with a fill tube 34 as shown in my Patent No. 4,326,426. The entire disclosures of said patents are incorporated herein by reference. A small diameter vent tube 40 extends onto the sample body to communicate with the interior 37 of the mold to provide a vent for the sample cavity 37 to promote filling of the sampler when the probe is immersed. A fusible cap 38 on the fill tube 34 is typically employed to prevent entry of molten metal while the probe is lowered through the slag. The tube 40 extends up above the surface 42 of the melt to ensure release of the air in the sample cavity as molten metal fills the cavity 37. The tube 40 can be connected to a cardboard float tube 46 which is adjustably positioned adjacent the upper end of the pipe 20 by clamp 48 for purposes hereinafter described.

The sample pod 30 can be releasably clamped to the weight 12 with a fusible clamp 52, such as a standard hose clamp. A fine braided stainless steel wire 54 with a knot 56 located inside of the sampler between the two mold halves anchors the wire 51 to the mold halves which are clamped together with a slight gap therebetween. The wire 54 extends through the interior 58 of the tube 40 to provide recovery of the sample mold 30. The molten steel fuses to wire and not to provide a secure connection to the sampler.

The tube 40 can be made of a small diameter paper board tube with an internal pressure 41. A tube having a diameter three sixteenths of an inch can be formed or bent to conform somewhat to the shape of the handle or pipe 20. Paper tape 4 can be used to releasably attach the tube to the pipe 20. The tube 40 also protects the wire. The tube 40 can be used with or without the wire to vent any sampler to a position above the molten metal. The vent tube 40 can be used with other immersion samplers such as that shown in U.S. Pat. No. 4,069,715, the entire disclosure of which is incorporated herein by reference. The vent tube 40 would be used instead of the vents 48 shown in FIG. 4 of that patent.

In use the entire assembly can be dropped by free fall into the steel with the lead wires and stainless wires connected or secured for retrieval. An ocean fishing reel 56 with built in drag and cable can be employed. The tension on the stainless wire of about ½ lb will cause the sampler pod to be jerked up when the fusible clamp releases. The reel 56 can be pre-set to go to 4 lbs tension after four second immersion to aid in quick removal of the pod from the melt. Four seconds immersion is adequate time for taking measurements and forming a sample.

In use, the probe will be lowered manually into the BOF furnace through the aperture at the top into a suitable position with the weight 12 below the surface of the slag to provide an accurate reading. This is accomplished by manually manipulating the wires 28. The weight of the pipe 20 above the surfaces as a counterweight to balance the buoyancy caused by the metal displaced by the voids in the weight 12. The float 46 is adjustable along the length of the pipe 20 to ensure that the proper immersion depth will be obtained with the sensor, and the float will maintain the probe in a generally erect position to avoid having the lead wires 28 touch the surface of the molten metal which can damage the wires. The float keeps the pipe 20 from tipping. As soon as the float hits the melt or slag it will tend to "right" the pipe. During immersion the fusible link 52 will melt and release the pod 30 which will float up to the surface with the wire affording retrieval of the sample mold. The wire 54 can be contained on a spool mounted on a fishing reel 56 with a bail to clutch and declutch the wire from the spool.

I claim:

1. A probe insertable in molten metal bath for analysis thereof comprise a sensor with connecting leads, a first weight, a second weight remote from said first weight, said first weight being the submersible portion of said probe and said second weight being a counterweight with a portion of the counterweight above the upper surface of the melt, said first weight having a cavity for supporting said sensor and a second cavity for said sensor connecting leads extending through said second weight, said second weight being connected to said first weight, a float attached on said second weight remote from said first weight, said first weight providing a buoyant force F1 and said second weight providing a compensating downward force F2, said forces F1 and F2 balanced to position the sensor at a selected depth in the molten metal beneath the surface, said float maintaining said probe in a generally vertical alignment with respect to said molten metal bath and preventing the probe from tipping into a position which could expose the leads to the molten metal and being damaged thereby, and said float limiting the depth of said first weight to a selected depth in the molten metal.

2. The probe of claim 1 wherein said second weight is an elongated relatively dense tube, said leads for said sensor extending through said tube.

3. The probe of claim 2 wherein said float is in the form of a paperboard tube adjustable positionable on said second weight tube.

4. The probe of claim 1 wherein said cavities in said first weight are sized to maximize the weight of the first weight and to provide a high weight-to-volume displacement for the first weight, and the length of said second weight is sized to provide a counterforce approximately equal to the buoyant force differential caused by the lesser specific gravity for density of the first weight, first weight cavity and sensor connecting leads cavity which ensure the immersion of the first weight below the molten metal at said selected depth.

5. A molten metal probe for obtaining data from a molten metal bath comprising a first weight having a cavity, a sensor having connecting leads supported in said cavity and being exposed to the molten metal bath, a second weight in the form of an elongated tube which is connected to said first weight; said sensor connecting leads extending through said elongated tube, said elongated tube having a portion positioned above the upper surface of the molten steel to provide a downward counter force to offset the buoyant force; to provide an equilibrium of the probe with the sensor positioned at an appropriate selected depth in the molten metal, and to provide reliable readings; and a float at the upper end of said elongated second weight to maintain the upper end of said elongated tube above the upper surface of the molten metal and of the slag to maintain the probe in a generally vertical position while immersed in the bath and to protect said sensor connecting leads from contacting the molten metal.

6. A molten metal probe for obtaining data from a molten metal bath comprising a first weight having a cavity, a sensor supported in said cavity and being exposed to the molten metal bath, a second weight in the form of an elongated tube which is connected to said first weight, said elongated tube having a portion above the upper surface of the molten metal to provide a downward counter force to offset the buoyant force and to provide an equilibrium of the probe with said sensor, said sensor being positioned at an appropriate depth in said molten metal to provide reliable readings.

* * * * *

UNITED STATES PATENT AND TRADEMARK OFFICE
CERTIFICATE OF CORRECTION

PATENT NO. : 4,881,824
DATED : November 21, 1989
INVENTOR(S) : Richard A. Falk and James Colzani It is certified that error appears in the above—identified patent and that said Letters Patent is hereby corrected as shown below:

Column 4, line 53:
  Delete "comprise" and substitute --- comprises ---.

Column 5, line 12:
  Delete "cavities" and substitute --- cavity ---.

Column 5, line 13:
  Delete "are" and substitute --- is ---.

Column 5, line 18:
  Delete "for" and substitute --- or ---.

Signed and Sealed this

Twelfth Day of May, 1992

Attest:

DOUGLAS B. COMER

*Attesting Officer*         *Acting Commissioner of Patents and Trademarks*